US007736312B2

(12) United States Patent
Taylor et al.

(10) Patent No.: US 7,736,312 B2
(45) Date of Patent: *Jun. 15, 2010

(54) ACOUSTIC MONITORING SYSTEM

(75) Inventors: Terri K. Taylor, Marlborough, MA (US); Meir Rosenberg, Newton, MA (US); Rainuka Gupta, Cambridge, MA (US); Stephen Ferrer Wilson, Raynham, MA (US); Pierre S. Ostiguy, Rochester, MA (US); Bertil Romner, Lund (SE); Alan J. Dextradeur, Franklin, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1385 days.

This patent is subject to a terminal disclaimer.

(21) Appl. No.: 10/762,963

(22) Filed: Jan. 22, 2004

(65) Prior Publication Data
US 2005/0004460 A1    Jan. 6, 2005

Related U.S. Application Data

(63) Continuation of application No. 10/328,748, filed on Dec. 23, 2002, now Pat. No. 6,685,638.

(51) Int. Cl.
*A61B 8/00*    (2006.01)

(52) U.S. Cl. .................. 600/437; 600/407; 600/410; 600/309; 600/300; 367/7; 367/11; 367/130; 367/138; 73/625; 73/626; 73/700; 73/708; 73/171; 73/716; 607/30; 607/31; 607/32; 607/33; 607/60; 607/61

(58) Field of Classification Search ......... 600/407–471; 367/7, 11, 130, 138; 607/30–33, 60, 61
See application file for complete search history.

(56) References Cited

U.S. PATENT DOCUMENTS

| 4,378,809 | A | 4/1983 | Cosman |
| 4,595,390 | A | 6/1986 | Hakim et al. |
| 4,660,568 | A | 4/1987 | Cosman |
| 5,176,153 | A | 1/1993 | Eberhardt |
| 5,891,180 | A | 4/1999 | Greeninger et al. |
| 6,044,301 | A | 3/2000 | Hartlaub et al. |
| 6,067,473 | A | 5/2000 | Greeninger et al. |
| 6,070,102 | A | 5/2000 | Hartlaub et al. |

(Continued)

FOREIGN PATENT DOCUMENTS

JP    58146334 A    8/1983

(Continued)

*Primary Examiner*—Brian Casler
*Assistant Examiner*—John F Ramirez
(74) *Attorney, Agent, or Firm*—Nutter McClennen & Fish LLP

(57) ABSTRACT

An acoustic monitoring system that is able to verify the success or failure of the positional adjustment of a valve without the need for additional energy during non-invasive reprogramming is provided. The acoustic monitoring system includes a programmer for generating a sequence of commands to adjust the valve mechanism, and for receiving acoustic signals for analysis, a transmitter to implement the command and adjust the valve, and a sensor for detecting an acoustic signal generated from the valve during execution of the commands. A method for using the acoustic monitoring system is also provided.

19 Claims, 12 Drawing Sheets

U.S. PATENT DOCUMENTS

| | | |
|---|---|---|
| 6,082,367 A | 7/2000 | Greeninger et al. |
| 6,432,050 B1 * | 8/2002 | Porat et al. ................. 600/300 |
| 6,533,733 B1 * | 3/2003 | Ericson et al. .............. 600/561 |

FOREIGN PATENT DOCUMENTS

| | | |
|---|---|---|
| JP | 63158308 A | 7/1988 |
| JP | 5300941 A | 11/1993 |
| JP | 2000350708 A | 12/2000 |
| JP | 2001170162 A | 6/2001 |
| NL | 9 401 256 | 3/1996 |

* cited by examiner

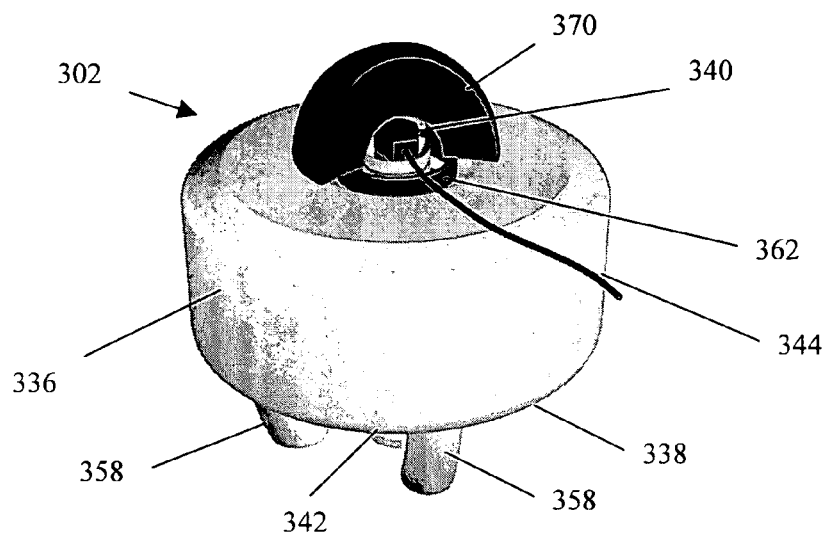
FIG. 5A
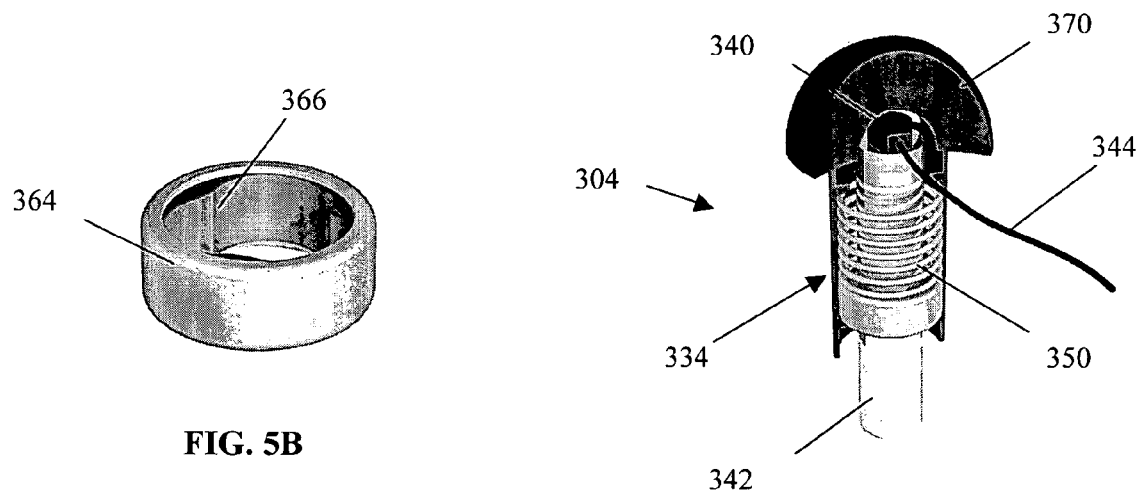
FIG. 5B
FIG. 5C

ACOUSTIC MONITORING SYSTEM

CROSS-REFERENCE TO RELATED APPLICATIONS

This application is a continuation of U.S. patent application Ser. No. 10/328,748, filed on Dec. 23, 2002.

STATEMENT REGARDING FEDERALLY SPONSORED RESEARCH

Not Applicable.

FIELD OF THE INVENTION

The present invention relates to methods and devices for non-invasively monitoring the performance of implanted medical devices without requiring additional energy means such as x-ray, ultrasound, or telemetry. More specifically, the present invention relates to a method for detecting the activity of an implanted adjustable shunt valve using an acoustic monitoring device and system.

BACKGROUND OF THE INVENTION

Shunt systems for directing body fluid from one region to another are known in the medical field. One application for such a shunt system is in the treatment of hydrocephalus, a condition where cerebrospinal fluid collects in the ventricles of the brain of a patient. Cerebrospinal fluid is produced by the ventricular system and is normally absorbed by the venous system. However, if the cerebrospinal fluid is not absorbed, the volume of cerebrospinal fluid increases thereby elevating the patient's intracranial pressure. This excess cerebrospinal fluid can result in abnormally high epidural and intradural pressures. Left untreated, hydrocephalus can result in serious medical conditions, including subdural hematoma, compression of the brain tissue, and impaired blood flow.

To treat patients with hydrocephalus, shunt systems have been used to remove the excess cerebrospinal fluid and to discharge the fluid to another part of the patient's body, such as the right atrium or peritoneal cavity. By draining the excess fluid, the elevated intracranial pressure is relieved. Generally, these fluid shunt systems include a valve mechanism for controlling or regulating the flow rate of fluid through the shunt system. The shunt systems often include a brain ventricular catheter in fluid communication with the valve mechanism. The ventricular catheter is inserted into a ventricle of the brain and a peritoneal catheter, which is also in fluid communication with the valve mechanism, is inserted into the peritoneal cavity of the patient for discharging the excess cerebrospinal fluid. The valve mechanisms of these shunt systems typically operate to permit fluid flow only once the fluid pressure reaches a certain threshold level. The fluid flow rate is proportional to the pressure at the valve mechanism. Thus, for a pressure slightly greater than the threshold or opening pressure, the flow rate is relatively low. As the pressure increases the flow rate through the shunt system concomitantly increases. At pressures significantly greater than the threshold pressure, a maximum flow rate for the system is reached. Fluid flow normally continues until the intracranial pressure has been reduced to a level less than the threshold pressure, subject to any hysteresis of the device.

The threshold or opening pressure that allows fluid flow through a shunt system must often be adjusted. For example, a surgeon may initially select a relatively low opening pressure to trigger fluid flow. Over time, the initial opening pressure may not be ideal. For example, it could lead to excess fluid flow, creating an undesirable overdrainage condition in which too much fluid is drained from the ventricle. Such a situation may give rise to a need to increase the opening pressure to produce a fluid flow rate that is balanced to avoid both excessive intracranial pressure and overdrainage conditions.

Because physiologies will vary over time and from one individual to another, some valve systems have been designed to be adjustable without requiring invasive procedures. These adjustable valves allow the clinician to customize the implanted valve mechanism's opening pressure for a particular patient, without the need to surgically remove the implanted shunt system, adjust the valve mechanism, and then surgically implant the shunt system again. Such an adjustable valve system is described in, for example, U.S. Pat. Nos. 4,595,390, 4,615,691, 4772,257, and 5,928,182, all of which are hereby incorporated by reference. Commonly referred to as the Hakim programmable valve, the Hakim valve described in these patents is a differential pressure valve with very precise opening pressures determined by the force exerted on a ruby ball in a ruby seat. The pressure at which the valve opens can be adjusted non-invasively by the clinician by means of an externally applied rotating magnetic field. The valve opening pressure is adjusted by varying the spring tension exerted on the ruby ball. Applying an external magnetic field to energize the soft magnet stator components of the valve initiates the adjustment cycle. The magnetic field causes the rotor to rotate about a central axis. As the stator polarity is cycled, the rotor (cam) moves to different positions to align with the stator. These components perform together as a stepping motor. The spring rides along the cam; as the cam rotates clockwise or counter-clockwise, the spring tension increases or decreases, respectively. Other exemplary types of adjustable shunt valves are described in U.S. Pat. Nos. 5,637,038 and 5,643,194.

Current practice recommends an x-ray be taken after each valve adjustment to verify the new setting. The use of additional energy means to conventionally determine valve position, however, can often lead to undesirable complications. For instance, when magnetic fields are used for verifying valve position, metallic equipment within the clinical environment may interfere with the accuracy of information obtained through the use of these magnetic forces, leading to inaccurate readings.

There is thus a need for a non-invasive means of accurately verifying the position of an implanted adjustable valve within a patient so that repeated exposure of the patient to radiation energy is reduced or eliminated. Also desirable is a valve position verification device that is small, easy to use, and preferably portable. Preferably, the device can also monitor various valve functions without the necessity for additional energy means.

SUMMARY OF THE INVENTION

The present invention achieves the aforementioned goals by providing an acoustic monitoring system that is able to verify the valve positions of an implanted adjustable valve having a variable opening pressure, without the need for x-rays. The acoustic monitoring system is based on the observation that the mechanical motion due to the movement of the valve components sets up vibrations that lead to acoustic energy. Acoustic energies have been noted by listening to audible emissions while adjusting the valve. Accordingly, the present invention provides the clinician with an immediate indicator of the success or failure of an adjustment cycle by monitoring the acoustic energies generated by the valve during that adjustment cycle. The monitored energy is correlated with the command sent to the valve to determine the success or failure of the valve adjustment.

In one aspect of the present invention, a method is provided for verifying the position of a valve mechanism in an adjustable programmable valve in a patient. First, an acoustic monitoring system is provided. The acoustic monitoring system includes a programmer for generating a sequence of commands to adjust an opening pressure of the valve mechanism. The programmer is electronically coupled to a transmitter for receiving the commands, which transmitter is also electronically coupled to a sensor for detecting an acoustic signal generated from the valve mechanism during execution of the commands. Then, the location of the valve mechanism of the implanted valve is determined by the clinician. The transmitter is positioned over the valve mechanism and the sequence of commands from the programmer is initiated. The commands are sent to the transmitter, which then adjusts the valve mechanism accordingly. The acoustic signal generated from the valve is then detected by the sensor and transmitted back to the programmer. The programmer then analyzes the acoustic signal to confirm the position of the valve mechanism. Preferably, the programmer of the acoustic monitoring system generates an audible signal to confirm the success or failure of the adjustment. Visual confirmation can also be achieved by way of a message displayed on a panel or LCD.

To adjust the opening pressure of the valve mechanism, the sequence of commands from the programmer directs the transmitter to generate a magnetic field and apply this magnetic force to the valve mechanism. The valve mechanism can be of the type having a stepped motor, whereby adjustment is achieved by rotating the stepped motor. As the valve mechanism is moving, an acoustic signal is generated which is picked up by the sensor and translated to an electronic signal. The electronic signal can be relayed back to the programmer for analysis. The programmer can include a microprocessor for running a software that applies an algorithm for translating the acoustic signal into information for determining the success or failure of the adjustment cycle. The algorithm can classify the acoustic signal into clicks, bangs or other, for example. The algorithm then compares the actual streams of clicks and bangs detected from the transmitter to an expected stream of clicks and bangs to determine the success or failure of the adjustment cycle.

Once the programmer is done analyzing the electronic signal, an audible signal can be produced to indicate whether or not the command was properly executed. To maximize the ability of the sensor to detect the acoustic signal, ultrasound gel can be applied on the patient prior to positioning the transmitter. In one exemplary embodiment of the present invention, the sensor can be inserted into the transmitter after it has been positioned on the patient and over the valve mechanism.

In another aspect of the present invention, an acoustic monitoring device is provided for verifying the position of a valve mechanism in an adjustable programmable valve in a patient. The acoustic monitoring device comprises a housing having a top surface, a bottom surface, and a central opening extending through the bottom surface. A transmitter is contained within the housing. The transmitter has a plurality of electromagnetic coils for generating an electromagnetic field sufficient to rotate the valve mechanism of the adjustable programmable valve. The housing can have stainless steel feet extending from the bottom surface to help focus the electromagnetic field onto the valve mechanism. A tubular coupling member extends through the central opening of the housing. Seated on top of the tubular coupling member is an acoustic sensor, which is capable of detecting an acoustic signal generated by the valve mechanism during adjustment. The acoustic signal can be of the type consisting of bangs and clicks.

In other features of the present invention, the tubular coupling member extends beyond the bottom surface of the housing, and is configured to contact the patient's skin. Furthermore, the acoustic sensor is mechanically isolated from the transmitter. Mechanical isolation can be achieved by having isolating pads or o-rings surrounding the outer diameter of the tubular coupling member. The isolating pads on the tubular coupling member prevent mechanical vibration of the housing from being transferred to the sensor. Yet another feature of the present invention is that the acoustic sensor can be configured to be inserted into the housing after the housing is positioned over the valve mechanism. In this way, the acoustic monitoring device can be modular, or built by the clinician during use. The tubular coupling rod can also be held in springing engagement within the housing, enabling movement with respect to the base of the housing. This feature allows self-adjustment of the coupling rod to the patient's anatomy and optimizes the contact between the sensor and the patient.

Additionally, the acoustic monitoring device can include a power source for driving the electromagnetic coils contained within the housing. A signal amplifier, digitizing filter, and data storage unit can also be included within the housing for downloading the acoustic signal information to the programmer for analysis. Furthermore, the acoustic monitoring device can be configured for wireless communication for wirelessly transmitting the acoustic signal information to the programmer. For example, a wireless communication transmitter can be connected to the transmitter of the acoustic monitoring device to allow wireless transmission of the acoustic data to the programmer for analysis.

BRIEF DESCRIPTION OF THE DRAWINGS

The invention can be more fully understood from the following detailed description taken in conjunction with the accompanying drawings, in which:

FIG. 5A shows a partial cutaway view of another embodiment of the acoustic sensor device of the present invention;

FIG. 5B shows an enlarged view of the retaining ring of the acoustic sensor device of FIG. 5A;

FIG. 5C shows an enlarged view of the acoustic sensor of FIG. 5A;

DETAILED DESCRIPTION OF THE INVENTION

Figure 1A:
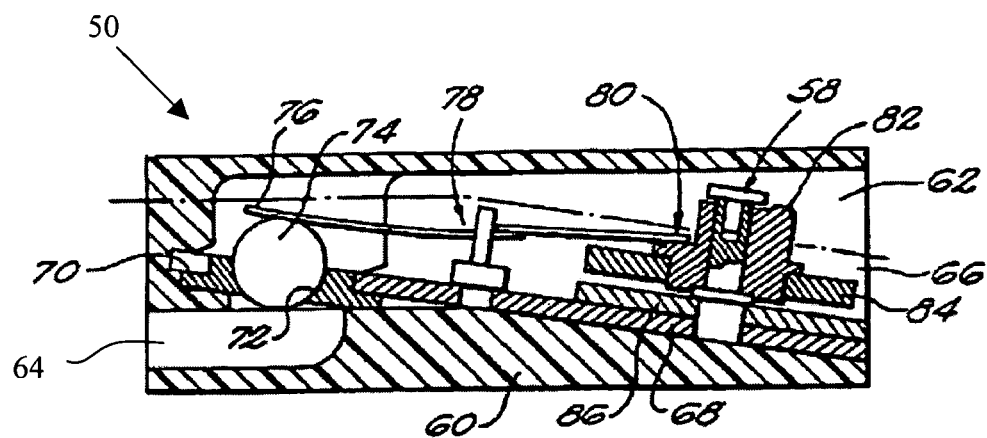
FIG. 1A is a side, sectional view of a prior art externally programmable shunt valve.

By way of introduction, FIG. 1A shows a prior art externally programmable shunt valve system 50. The shunt valve 50 is typically surgically implanted under the scalp of a patient. The shunt valve 50 includes a valve body 60 defining a chamber 62 with an inlet opening 64 and an outlet opening 66. When a fluid pressure at the inlet opening exceeds the predetermined threshold, fluid begins to flow through the shunt valve via the inlet and outlet openings 64, 66. A support plate 68 is disposed within the valve body 60 and includes an aperture 70 at one end that is provided with a valve seat 72. A ball 74 is adapted for sealing engagement with the valve seat 72. A first end 76 of a spring 78 biases the ball to the valve seat 72 to prevent fluid flow. The biasing force of the spring 78 is adjustable by varying the vertical position of the spring at a second end 80, which can be adjusted by means of a cam 82. The cam 82 includes a plurality of steps of varying vertical position with respect to the plate 68. Each step provides a discrete pressure on the ball 74 via the spring 78. The biasing force provided by the spring 78 determines the threshold pressure that must be overcome in order to separate the ball 74 from the valve seat 72 and allow fluid flow into the chamber 62.

The cam 82 is disposed in a centrally located hole in a rotor 84 which includes a plurality of permanent magnetic poles of alternate polarity. At any one angular position, a pole exposed on the top side has an opposite pole on the other side. Below the rotor 84, four stator elements are fixed in a stator member 86. The stator elements are formed from a magnetically soft and permeable material. The stator elements are shaped to conform to the rotor 84 elements.

Figure 1B:
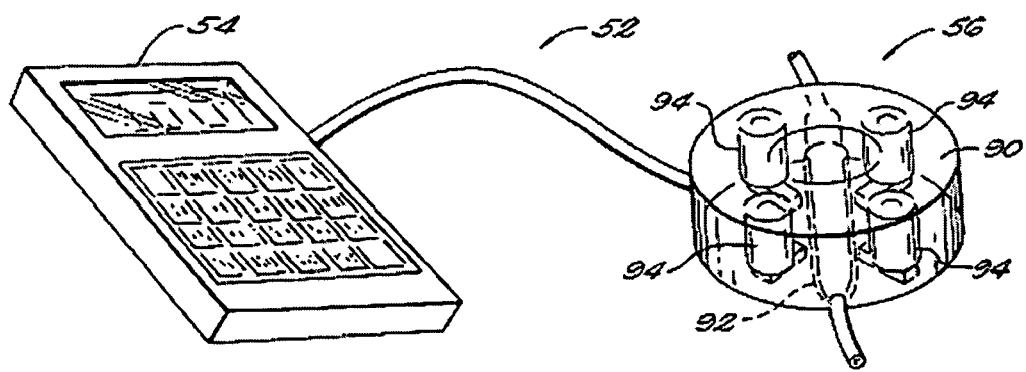
FIG. 1B is a perspective view of a prior art programmer for programming the prior art shunt valve of FIG. 1A.

After surgical implantation of the shunt valve 50 under the scalp of the patient, the threshold pressure can be adjusted. FIG. 1B shows a prior art external programming device 52 for adjusting an opening pressure at which fluid begins to flow through the adjustable valve system 50. The programming device 52 includes a control device 54 for selecting a threshold pressure and a programming element 56 that is placed over the scalp protrusion that is created by the implanted shunt valve. The programming element 56 includes a housing 90 having a groove 92 adapted to conform to the protrusion. An operator maneuvers the programming element 56 so that the scalp protrusion is within the groove 92. Thereafter, a series of electromagnets 94 disposed about a central axis are sequentially energized to apply a pulsed magnetic field to the stepper motor and cause the rotor to rotate. This causes the cam 82 to rotate and therefore adjust the pressure applied to the ball 74 by the first end 76 of the spring. In this manner, the threshold or opening pressure of the shunt valve is adjusted.

After an adjustment is made to the shunt valve, current practice recommends an x-ray be taken after each valve adjustment to verify the new setting. The use of additional energy means to conventionally determine valve position is, however, undesirable. The patient's exposure to the radiation can often lead to harmful radiation build-up. Additionally, magnetic equipment within the clinical environment can often interfere with the accuracy of information obtained through the use of these magnetic forces, leading to inaccurate readings. The present invention avoids the aforementioned problems by providing an acoustic monitoring system which can operate to program the opening pressure of an implanted adjustable valve within a patient non-invasively, and which can verify the valve position after adjustment without the need for radiation.

Figure 2A:
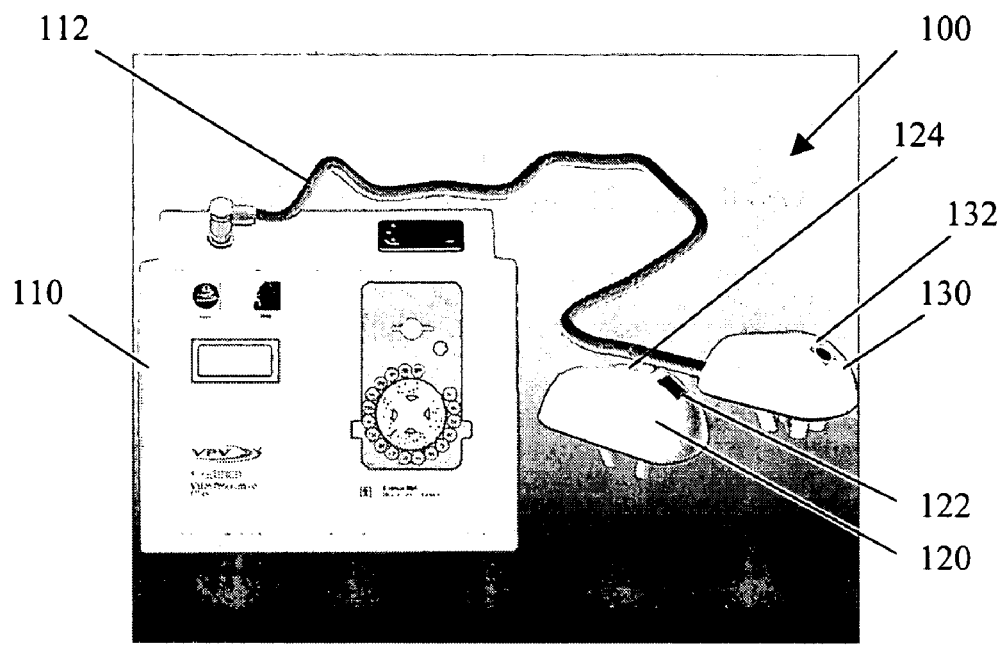
FIG. 2A is a perspective view of an exemplary acoustic monitoring system of the present invention.

As shown in FIG. 2A, an acoustic monitoring system 100 in accordance with the present invention is provided. To carry out the features of the present invention, the acoustic monitoring system 100 includes a programmer 110 which generates the commands to adjust the valve position of the adjustable valve. The programmer 10 houses the user interface, control programs, sensor amplification and processing elements, stepper drive circuitry, and power supplies. Preferably, the programmer 110 is small enough to be hand held and/or portable for the clinician's convenience. The commands are sent to a transmitter which then generates the magnetic field that actuates the movement of the valve stepper motor.

In the exemplary embodiment illustrated, the acoustic monitoring system 100 includes two transmitters: a first, viewing transmitter 120 which is used to visualize and identify the protrusion formed under the patient's scalp by the implanted valve through its central opening 124, and a second, implant transmitter 130 for monitoring the motion of the valve mechanism. As shown in FIG. 2A, the second transmitter 130 can be connected directly to the programmer 110 via transmitter cable 112 as shown. While not illustrated, it is understood that the first transmitter 120 can also include a transmitter cable for electrically coupling to the programmer 110 in the same manner.

Figure 2B:
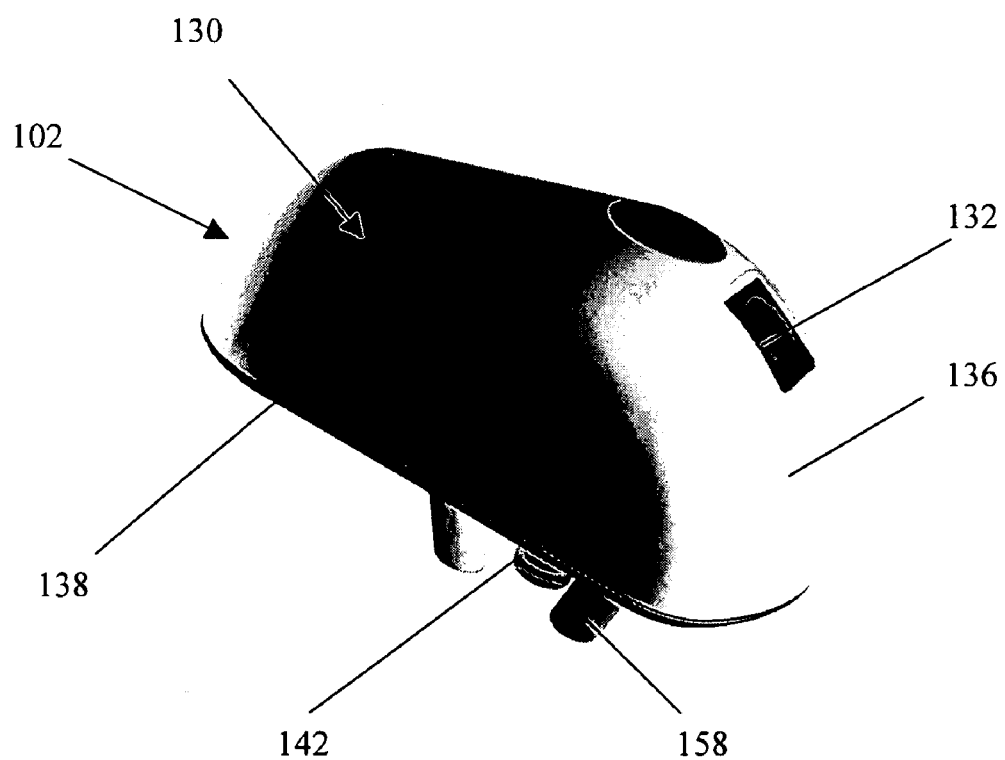
FIG. 2B is an enlarged view of a second transmitter of the acoustic monitoring system of FIG. 2A.

The first and second transmitters 120, 130 each include an adjustment cycle start button 122, 132. As shown in FIG. 2B, the cycle start button 132 can be configured as a momentary switch having a depressed finger region. Each of the first and second transmitters 120, 130 houses coils (such as coils 150 shown in FIG. 3A) that are required to create the magnetic field that energizes the valve stepper motor. In one embodiment, the first and second transmitters 120, 130 can include four coils, with each coil wired in series as a pair. Each transmitter 120, 130 can also include a temperature sensor to ensure that the coils do not generate too much heat and endanger the patient's comfort and safety. Additionally, each transmitter 120, 130 can also contain illumination means such as LEDs that can illuminate the work area to help the clinician better visualize the scalp protrusion and implanted valve during positioning of the transmitters 120, 130.

Figure 3A:
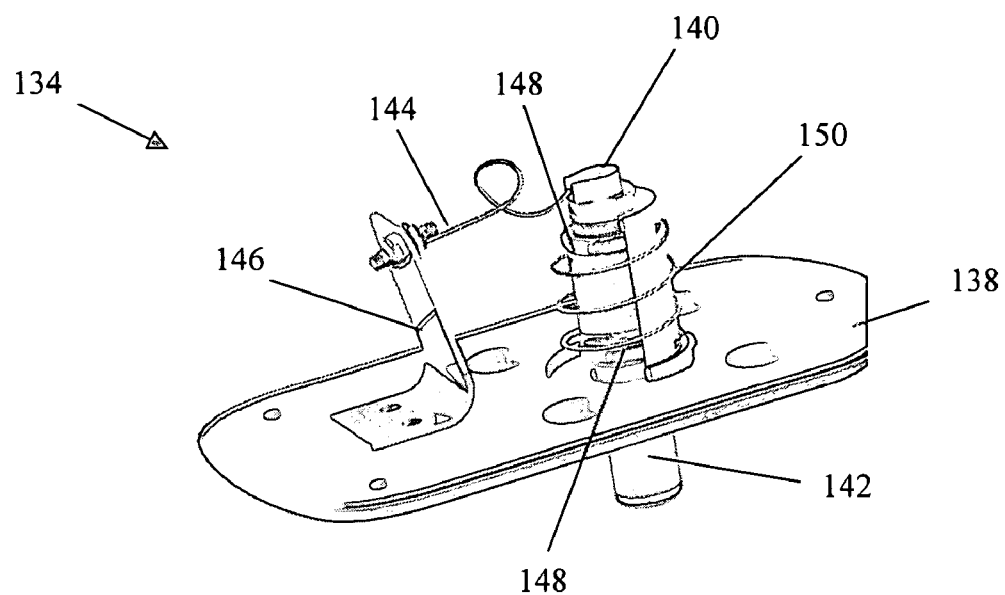
FIG. 3A is a perspective view of the sensor assembly within the transmitter assembly of the second transmitter of FIG. 2B.
Figure 3B:
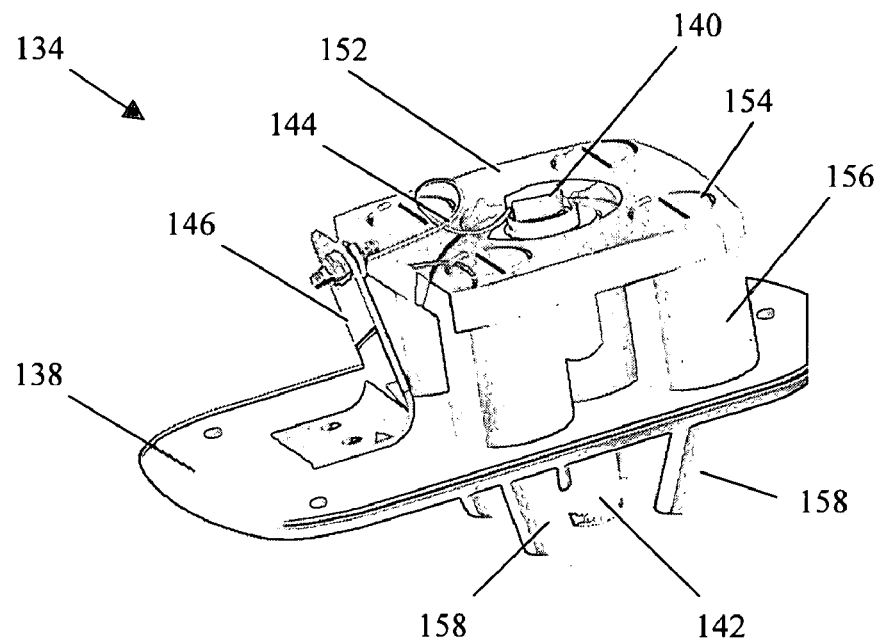
FIG. 3B is yet another perspective view of the transmitter assembly of the second transmitter of FIG. 2B.

Turning now to FIGS. 3A and 3B, the second transmitter 130 also provides support, guiding means and alignment for an acoustic sensor 140. The acoustic sensor 140 picks up the acoustic signals generated from the valve mechanism during the adjustment cycle. As shown, the acoustic sensor 140 can be held within the assembly 134 of the second transmitter 130 and contained within its housing 136. The second, valve adjustment transmitter 130, together with its acoustic sensor 140, forms an acoustic monitoring device 102 of the present invention. The acoustic monitoring device 102 is a one-component transmitter and signal detector that serves to program the adjustable valve as well as detect the motion of the valve during adjustment.

The acoustic sensor 140 can be connected to an acoustic amplifier which itself can be connected to a signal filter. Both the signal filter and the programmer 110 can be connected to a connection box. Additionally, the programmer 110 can be connected to an isolation transformer which, along with the connection box, are connected to a monitor and/or recording system as is well known in the art. In the preferred embodiment illustrated in FIG. 2A, the acoustic amplifier, signal filter, isolation transformer, monitor and/or recorder, and connection box are all contained within the programmer 110.

In use, the acoustic sensor 140 translates the acoustic energy generated by the valve mechanism during an adjustment cycle into an electric signal that is sent to the programmer 110 for processing. Preferably, the programmer 110 is electronically connected to the acoustic sensor 140, which detects the signal from the implanted valve during an adjustment cycle. The signal emitted from the valve is received and analyzed using a predetermined algorithm to provide information such as the position, performance, etc., of the adjustable valve. The algorithm processes and classifies the signals, for example, as a "click," "bang," or "other." By "other," what is meant is that the event did not meet the criteria required for classification as a "click" or a "bang." These classification events are then compared to the known expected behavior of the valve to determine the success or failure of the adjustment cycle. Alternatively, the acoustic sensor 140 can be used in a passive manner, i.e., without a programmer, to listen to and isolate a specific function of the shunt valve. An example would be the opening or closing of a shunt valve mechanism.

As depicted in FIGS. 3A and 3B, in one embodiment of the acoustic monitoring device 102, the acoustic sensor 140 can be held within the transmitter assembly 134 of the second transmitter 130 via a tubular coupling member 142. As shown in FIG. 3A, the acoustic sensor 140 sits on top of the coupling member 142 and can be electrically connected via an electrical lead 144 to a metal bracket 146 seated on the housing base 138 of the second, implant transmitter 130. Preferably, the housing base 138 is also formed from a non-magnetic metal such as aluminum. Surrounding the circumference of the coupling member 142 are isolating pads 148. The isolating pads 148 buffer the acoustic sensor 140 from external vibrations and can be configured as o-rings surrounding the outer surface of the tubular coupling member 142. A spring 150 surrounding the coupling member 142 allows the sensor 140 to move up and down to accommodate variations in patient anatomy. The spring 150 also optimizes the contact between the coupling member 142 and the patient. The entire transmitter assembly 134 shown in FIG. 3B is enclosed within the plastic housing 136 of the second transmitter 130. Surrounding the acoustic sensor 140 is a top plate 152 which is attached to the housing base 138 with screws 154 extending through posts 156. The top plate 152 can comprise a metal such as stainless steel and, together with the feet 158, encloses the magnetic field generated around the posts 156 (which can house coils for generating the magnetic field). Extending from the housing base 138 are a plurality of feet 158 for resting and balancing the housing 136 against the patient and over the implanted valve. These feet 158 also help focus the magnetic field that actuates the valve mechanism.

As described above, the acoustic monitoring system 100 can include two different transmitters: one that has a central opening 124 for visual valve position verification, and a second one that does not have a central opening but instead has an acoustic sensor 140 coupled thereto. In the present embodiment, it is contemplated that the clinician could use the first transmitter 120 to adjust the valve mechanism prior to implantation, then use the second transmitter 130 when adjustment is required after implantation. While the acoustic monitoring system 100 of the present embodiment is shown and described as a two-transmitter system, it is contemplated that the acoustic monitoring system 100 can operate as a single-transmitter system, with the programmer 110 being used in combination with either the first or the second transmitter 120, 130, depending on the needs of the clinician. Alternatively, the acoustic monitoring system 100 can include a single transmitter that combines the functions of both the first and second transmitters 120, 130.

Figure 4A:
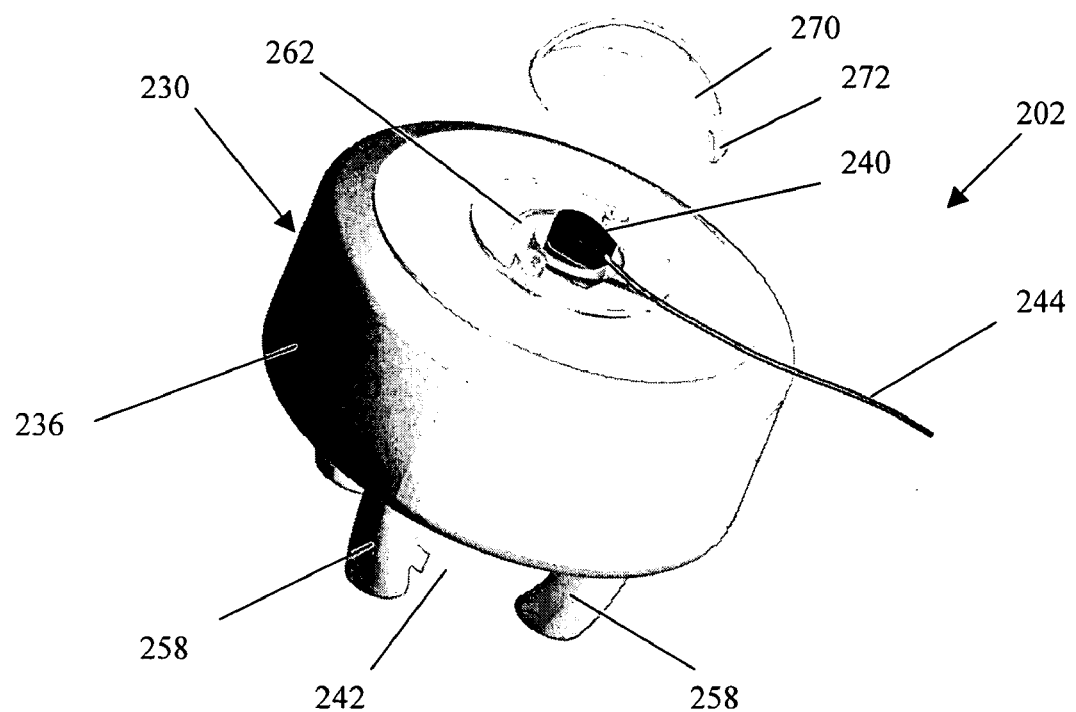
FIG. 4A shows a perspective view of an acoustic sensor device of the present invention.
Figure 4B:
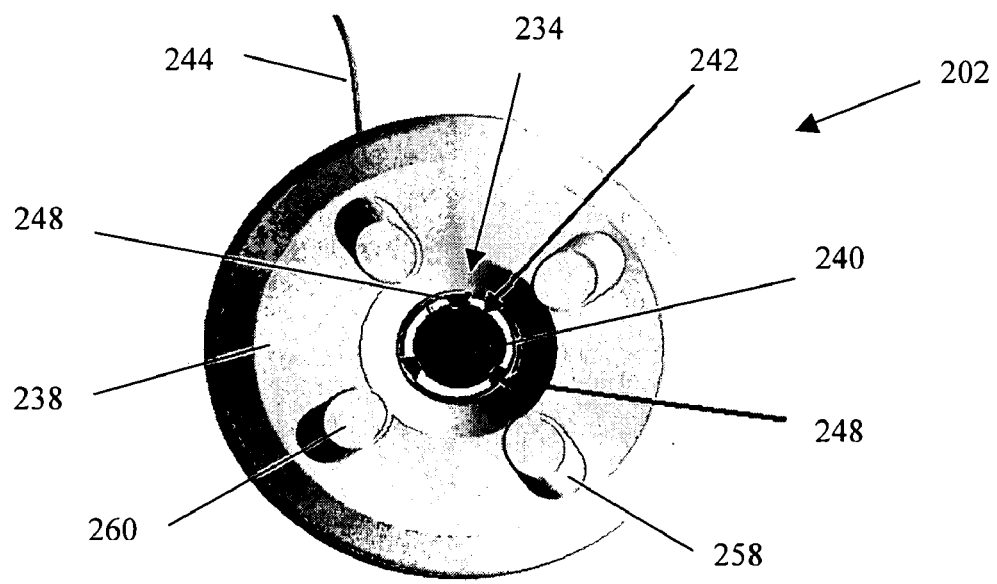
FIG. 4B shows a bottom view of the acoustic sensor device of FIG. 4A.

FIGS. 4A and 4B illustrate another exemplary embodiment of the acoustic monitoring device of the present invention. As shown, second transmitter 230 includes an acoustic sensor 240 within its housing 236. Collectively, the second valve adjustment transmitter 230 with its enclosed acoustic sensor 240 forms an acoustic monitoring device 202 of the present invention. As with the previous embodiment, the acoustic sensor 240 translates the acoustic energy generated by the valve mechanism into an electric signal that is sent to the programmer 110 for processing during a valve adjustment cycle. The acoustic sensor 240 can be configured to be held within the second transmitter 230 via a tubular coupling member 242. The acoustic sensor 240 and its coupling member 242 can be incorporated into the second transmitter assembly 234 as depicted in FIG. 4B to collectively form an acoustic monitoring device 202. Preferably, the programmer 110 is electrically connected to the acoustic sensor 240 via an electrical lead 244. The signal emitted from the device 202 is received and interpreted using a predetermined algorithm in the same manner described for the acoustic monitoring device 102.

In this exemplary embodiment of the second transmitter 230 of a two-transmitter acoustic monitoring system 100, the illustrated acoustic monitoring device 202 has an acoustic sensor 240 that is held on top of a tubular coupling member 242 that extends through a central opening 262 of the second transmitter 230. The coupling member 242 contacts patient skin and isolates the sensor 240 from environmental influences such as vibration and magnetic fields, which can affect the sensor's ability to read the acoustic signals. The acoustic sensor 240 can be seated on top of the coupling member 242. The coupling member 242 has isolating pads or o-rings 248 which surround the outer surface of the coupling member 242. As shown, the isolating pads 248 are spaced equidistantly around the circumference of the coupling member 242. The isolating pads 248 buffer the acoustic sensor 240 from external vibrations such as vibrations of the transmitter 230 or the hand motion of the clinician. Alternatively, mechanical isolation of the acoustic sensor 240 can be achieved using low durometer O-rings to maintain the sensor 240 within the coupling member 242. For instance, soft silicone O-rings can be suitable for this purpose. The O-rings should be as compliant as possible to maintain isolation, but be strong enough to move the sensor 240 and coupling member 242 together when conforming to patient anatomy.

Surrounding the second transmitter 230 is a housing 236. The housing 236 sits on top of housing base 238. A plurality of feet 258 can extend from the housing base 238 for resting and balancing the housing 236 against the patient and over the implanted valve. These feet 258 help focus the magnetic field that actuates the valve mechanism. The four feet 258 shown in FIG. 4B each have a curved, rod-like shape with a flat contacting surface 260. It is understood that the number and geometry of the feet 258 can be varied without departing from the spirit of the invention. For example, the feet 258 can have rounded edges so as to avoid damage to the patient's skin upon contact. Additionally, the feet 258 can be cushioned at the ends for the comfort of the patient. Further, the feet 258 can extend from the housing base 238 of the housing 236 such as shown in FIG. 3B. Preferably, a thermistor can be incorporated into the any of the various transmitters 120, 130, 230 to assure that the temperature of the feet 258 does not exceed a particular temperature during patient or clinician contact.

As illustrated in FIG. 4A, a cap 270 may optionally be placed over the acoustic sensor 240 and attached to a top surface of the housing 236 for maintaining and protecting the acoustic sensor 240 within the housing 236. As shown, the cap 270 includes a groove 272 to allow the electrical lead 244 of sensor 240 to exit the cap 270, and may optionally be attached onto the housing 236 with screws, by similar fastening devices, or by frictional engagement.

FIGS. 5A-5C illustrate yet another embodiment of the acoustic monitoring device 302 of the present invention. In this exemplary embodiment, the cap 370 of the acoustic monitoring device 302 is attached to a transmitter assembly 334. Together with its magnetic coils 350, which generate the magnetic field necessary to actuate the programmable valve, the cap 370 and transmitter assembly 334 shown in FIG. 5C form a cage-like structure which surrounds tubular coupling member 342 and acoustic sensor 340. The combined transmitter assembly 334 and acoustic sensor 340, or transmitter-sensor unit 304, can be held within housing 336 by a retaining ring 364 similar to the one shown in FIG. 5B. The retaining ring 364 has a contoured geometry configured to mate with and seat the combined transmitter assembly and acoustic sensor unit 304. Some of the contoured geometry of the retaining ring 364 can be attributable to foam padding 366 surrounding the inner circumference of the retaining ring 364 that provides mechanical isolation between the transmitter assembly and the acoustic sensor unit. The retaining ring 364 is configured to seat within a central opening 362. As with the acoustic monitoring device 102 described above, housing 346 contains a plurality of feet 358 extending from the housing base 338 and a central opening 362 extending from a top surface all the way through housing 336. Central opening 362 enables visual observation during placement of the acoustic monitoring device 302 over the valve mechanism when adjusting the implanted valve. The feet 358 help focus the magnetic field generated by coils 350 of the transmitter assembly 334 onto the valve mechanism.

As described above, the acoustic monitoring device 302 can be a modular system that enables the clinician to "build" the acoustic monitoring device 302 during use. That is, after the clinician determines the location of the implanted valve mechanism, the housing 336 can be positioned over the scalp protrusion and valve mechanism, using the central opening 362 to visually observe the placement of the housing 336 and feet 358 on the patient. Once satisfied that the housing 336 and the central opening 358 are properly situated over the implanted valve mechanism, the clinician can then slide the retaining ring 364 into the central opening 362 and position the transmitter-sensor unit 304 within the retaining ring 364. If the device 302 is not properly positioned, or if the clinician wishes to reposition the acoustic monitoring device 302, the device 302 can be disassembled and the steps above repeated. In this manner, the acoustic monitoring device 302 combines both features of the first, viewing transmitter and the second, implant transmitter of a two-transmitter acoustic monitoring system into one single transmitter.

Figure 6A:
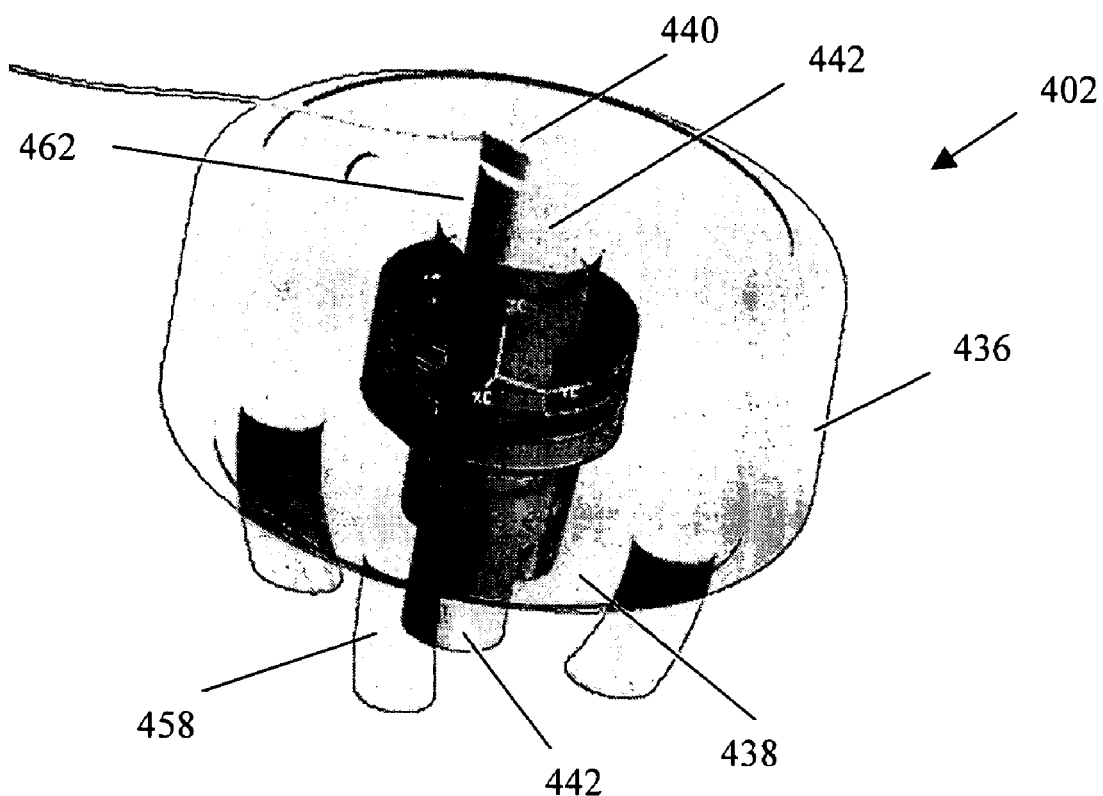
FIG. 6A shows a perspective view of yet another embodiment of the acoustic monitoring device of the present invention.

FIG. 6A represents yet another exemplary embodiment of a modular acoustic monitoring device 402 of the present invention. As with the previous embodiments, acoustic monitoring device 402 comprises a transmitter which includes a housing 436 having a housing base 438 from which a plurality of feet 458 extend. The feet 458 are effective to stabilize the device 402 on the patient and to focus the magnetic field on the valve mechanism. A central opening 462 extends through the housing 436 and enables the clinician to visually orient and position the device 402 over the implanted valve.

Figure 6B:
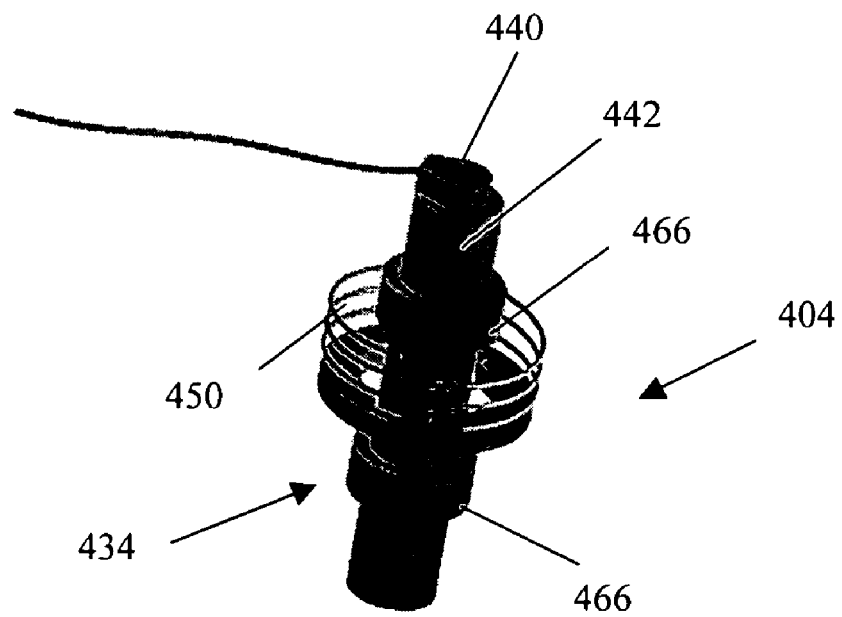
FIG. 6B shows an enlarged view of the transmitter and sensor of FIG. 6A.

FIG. 6B is a detailed view of the sensor unit 404 comprising a tubular coupling member 442, in which an acoustic sensor 440 is seated, and a spring 450 to provide mechanical isolation from the transmitter housing 436. The spring 450 also enables adjustment of the coupling member 442 for conforming to patient anatomy. The spring 450 also optimizes contact between the coupling member 442 and the patient. The coupling member 442 also includes a plurality of flanges 466 on its outer surface. Preferably, the transmitter-sensor unit 404 is inserted into the central opening 462 after the device 402 has been positioned over the implanted valve. In one aspect of the embodiment, sensor unit 404 can include flanges 466 located on the coupling member 442, as shown in FIG. 6B. These flanges 466 mate with grooves or indents (not shown) within the housing 436 to maintain the sensor unit 404 properly aligned with respect to the housing 436. Modular acoustic monitoring device 402 combines both features of the first, viewing transmitter and the second, implant transmitter of a two-transmitter acoustic monitoring system into one single transmitter.

In addition to the embodiments of the acoustic monitoring system 100 already mentioned, it is contemplated that the implant transmitter 130, 230, 330, 430 can also include components for signal amplification, filter digitizing, data storage, and a power source for driving the coils 150, 250, 350, 450 within the transmitter. The signal amplifier, digitizing filter, data storage unit, and power source, which are well known in the electrical art, would enable the transmitter to be free of the tether (i.e., electrical cable) to the programmer 110. For example, the programmer 110 can be configured to include a cradle (not shown) for seating the valve adjustment transmitter, allowing direct communication of the command stream from the programmer 110 to the transmitter. After the transmitter is programmed, the clinician can pick up the transmitter from the cradle, place the transmitter over the shunt valve and adjust the opening pressure of the valve mechanism, then replace the transmitter back into the cradle of the programmer 110. The acoustic data picked up by the transmitter can then be downloaded to the programmer 110 for further analysis. Alternatively, the transmitter can be configured for wireless connection to transmit via radiowave or infrared transmission the acoustic signal data as it is acquired from the implanted valve to the programmer 110. For instance, the transmitter can further be connected to a wireless communication transmitter for communicating with the programmer 110.

In other aspects of the present invention, suitable materials from which the housing 136, 236, 336, 436 can be formed include a medical grade plastic such as molded polycarbonate. Other suitable materials include aluminum, Teflon®, and Acetal (Delrin®). The feet 158, 258, 358, 458 extending from housing 136, 236, 336, 436 and its base 138, 238, 338, 438 can be made of a metal such as stainless steel. The acoustic sensor 140, 240, 340, 440 can be any transducer sensitive to vibration such as an accelerometer and its coupling member 142, 242, 342, 442 can be formed from polycarbonate (Lexan®). The isolating pads can be made from acoustic foam and the isolating o-rings from low durometer (40) silicone.

Figure 7A:
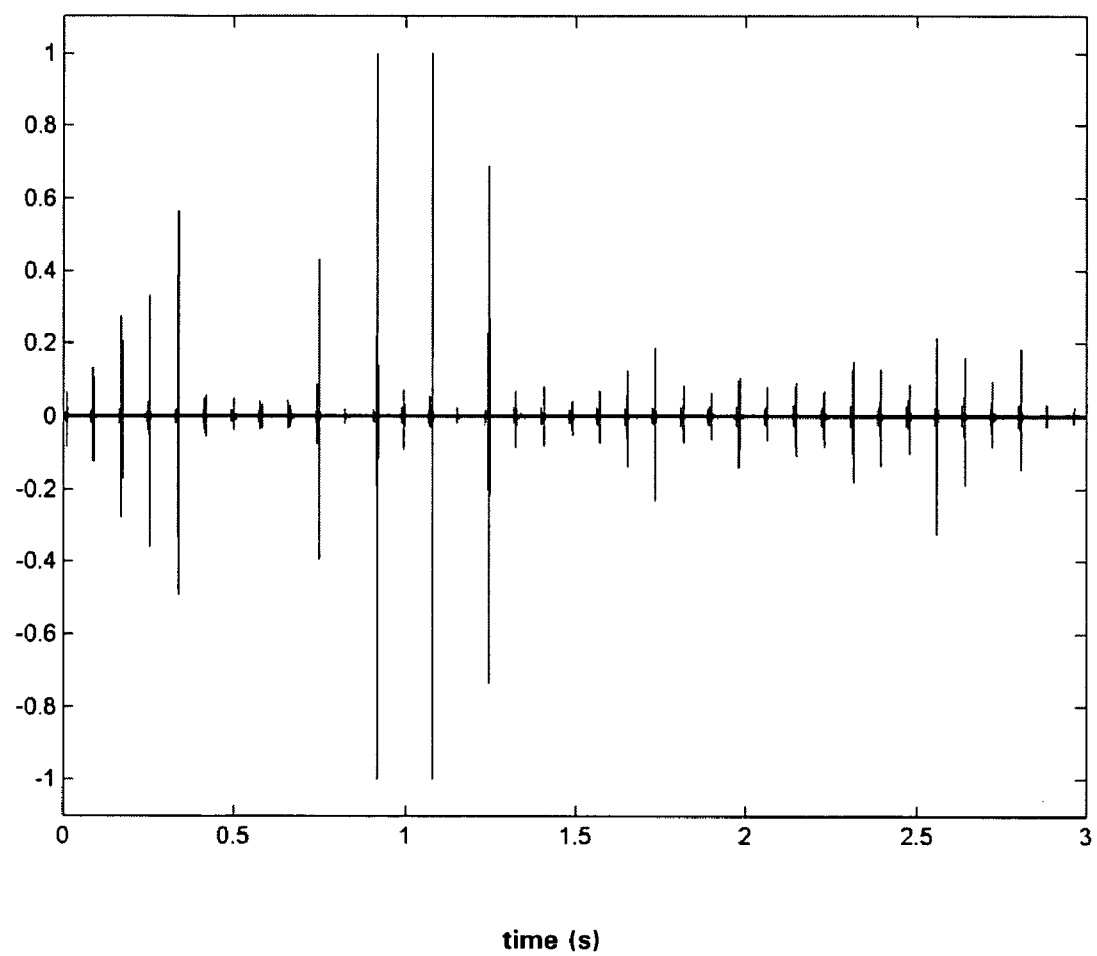
FIG. 7A graphically represents all acoustic events generated during a complete adjustment cycle.
Figure 7B:
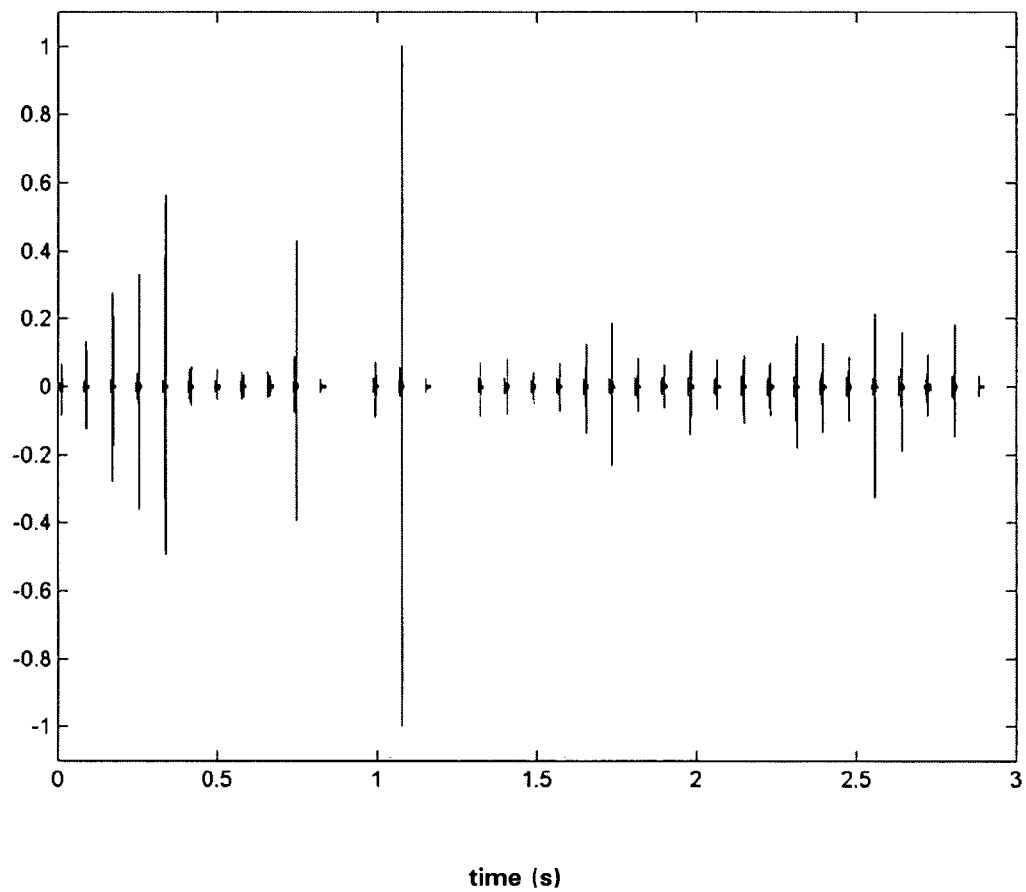
FIG. 7B graphically represents the click signals generated during a complete adjustment cycle.
Figure 7C:
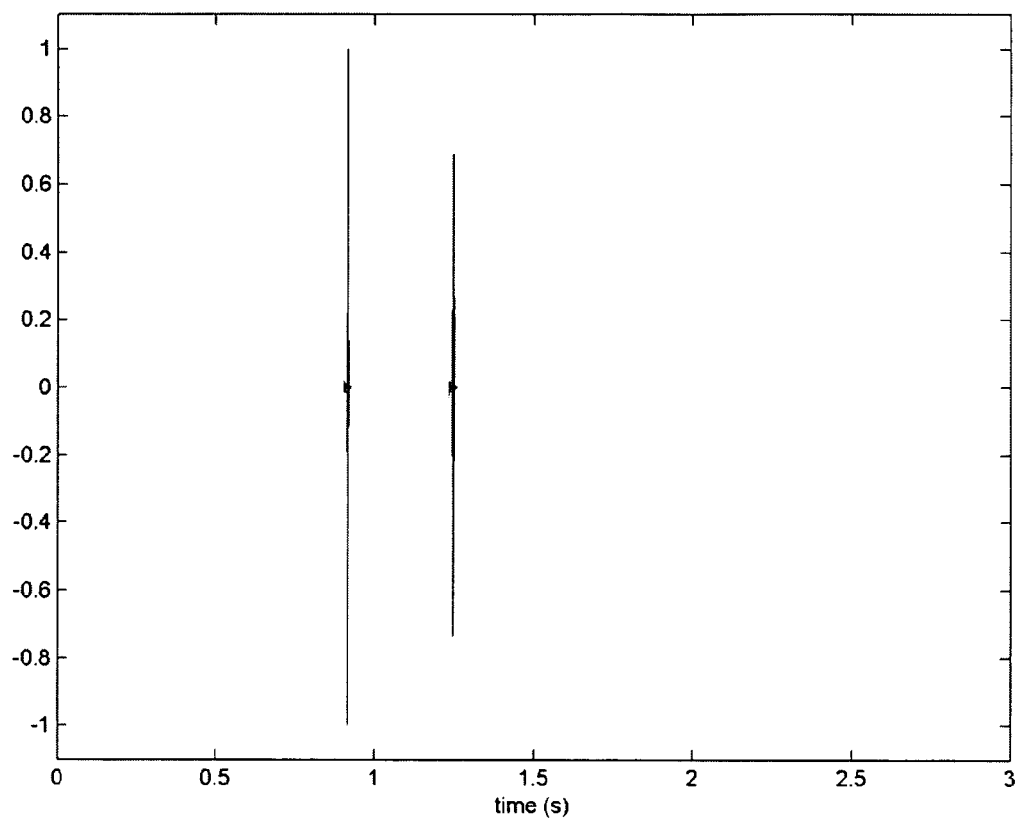
FIG. 7C graphically represents the bang signals generated during a complete adjustment cycle.
Figure 8:
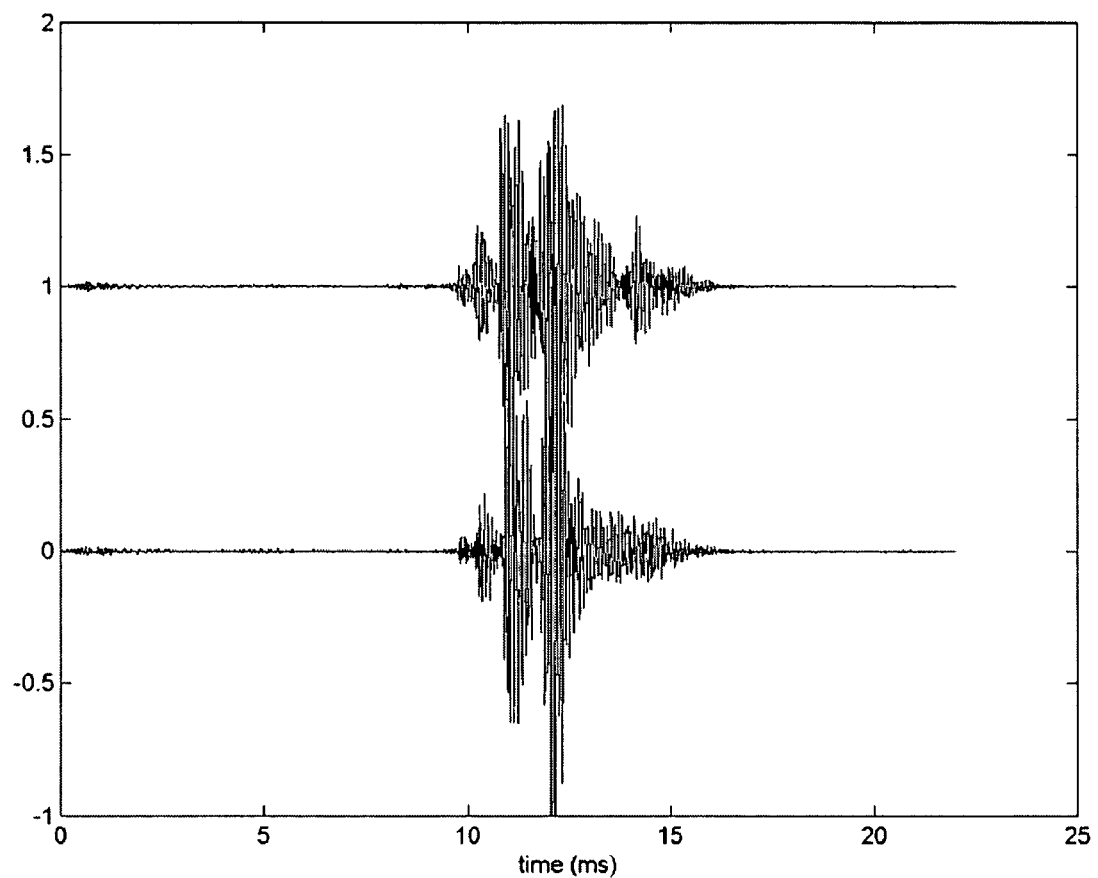
FIG. 8 represents exemplary bang signals generated in a programmable valve over time.
Figure 9:
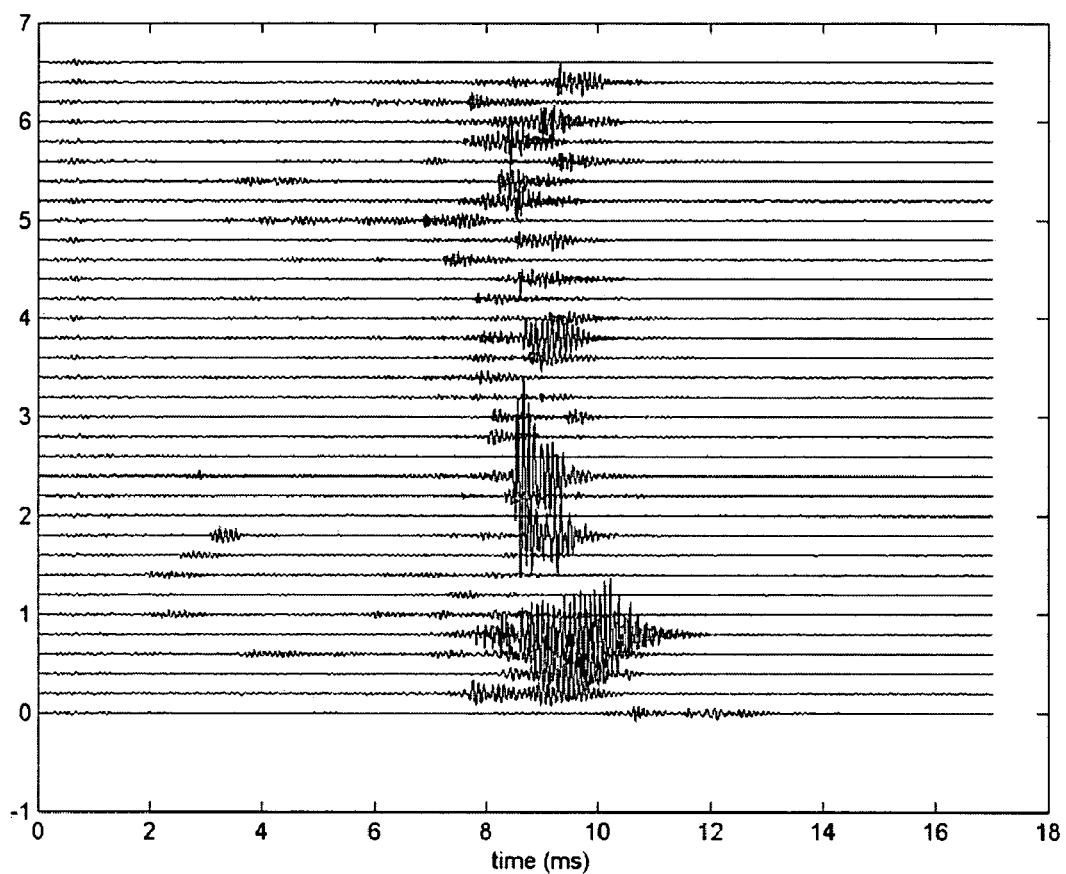
FIG. 9 represents exemplary click signals generated in a programmable valve over time.
Figure 10:
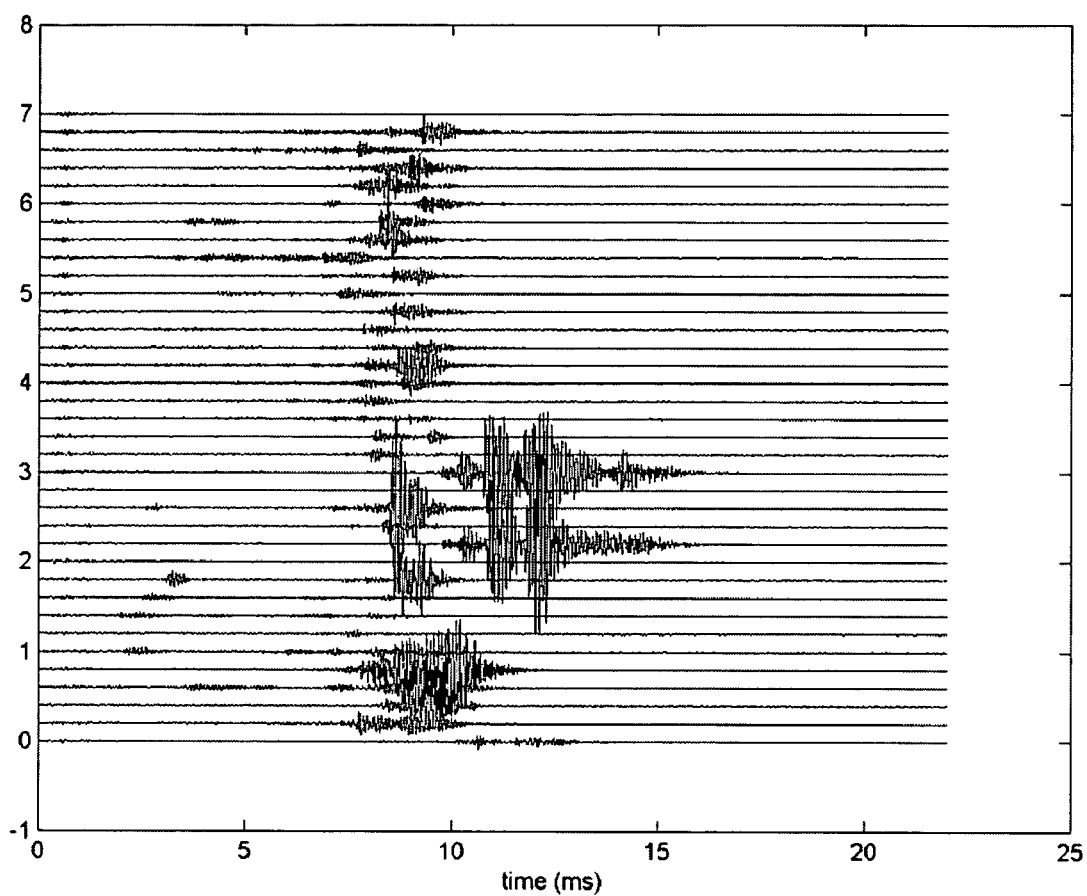
FIG. 10 represents all acoustic events generated in a programmable valve over time.

The acoustic monitoring system 100 of the present invention operates by identifying two types of acoustic events that occur during an adjustment cycle (the process associated with changing the opening pressure of a valve mechanism of a programmable valve): "clicks," an acoustic event associated with the motion of the valve spring along the rotor cam as it rotates clockwise (CW) or counterclockwise (CCW), and "bangs," an acoustic event associated with the cam as it rotates counterclockwise and reaches the mechanical limit. The "bang" signal can also indicate when the valve is in the "home" or starting position, i.e., the position on the cam where the spring is at the lowest level. The distinction between the two acoustic signals is graphically represented in FIGS. 7A-7C, wherein FIG. 7A represents all the acoustic events generated during a complete adjustment cycle for an exemplary programmable valve, FIG. 7B represents the click signals generated during a complete adjustment cycle, and FIG. 7C represents the bang signals during a complete adjustment cycle. As graphically shown in FIG. 8, bang events generated in an exemplary programmable valve over time are distinct from other signals (such as from the programmer or the environment). Click events generated in the valve over time are distinct and reproducible, as graphically depicted in FIG. 9. FIG. 10 represents all the acoustic events generated in the valve over time. By "all the acoustic events" what is meant is the combination of click and bang signals. Events that do not meet explicit criteria, meaning there is not enough signal energy, would not be classified as a "click" or a "bang."

In the present invention, the acoustic signal(s) are interpreted and analyzed to first classify the events as either "clicks," "bangs," or "other," and then a determination is made as to whether the valve mechanism has been properly adjusted. Preferably, there can be an audible indication of success or failure. For example, the acoustic monitoring system 100 can employ a piezo buzzer, where the acoustic monitoring system 100 makes one beep for success and three beeps for failure. Of course, it is understood that any variety of noise generators can be used to make the audible indication, and that the audible indication can take the form of any desirable sound, so long as the sounds are different for success and failure. Alternatively, the system 100 can provide a visual indication of success or failure. The visual indication can take the form of a message displayed on a panel or LCD, for instance. Visual confirmation can be used instead of, or in addition to, audible confirmation.

One having ordinary skill in the art will appreciate that a variety of programmers can be used in association with the present invention. By way of example, one useful programmer system 110 is described below.

Programmer

One exemplary programmer useful to carry out the adjustment cycle of the programmable valve is the Codman Model No. 82-3190 programmer currently used by clinicians to reprogram Hakim-type valves. An improvement to this programmer adds the electronics and processing required for the verification process. Such a programmer 110 operates as the command center of the acoustic monitoring system 100. The programmer 110 houses the user interface, controller board and power driver board. Each of these elements will be described in more detail below.

User Interface

The user interface component includes visual elements for operating the acoustic monitoring system 100, and includes a display panel, usually a liquid crystal display (LCD) for communicating instructions, program confirmation, configuration options and detected errors to the clinician. The display can have a 20 character×4 line format to accommodate various languages such as but not limited to English, French, German, Italian, Spanish, Portuguese, Finnish, Danish, Swedish, Dutch, Greek, and Japanese.

Associated with the programmer 110 is an array of eighteen keys representing the selectable valve opening pressures. These keys form a selection keypad similar to the one shown in FIG. 1B, which illustrates a known programmer 54 used for adjusting Hakim-type valves. When the keys are pressed during the first 3 seconds after power is turned on, configuration selection is enabled. It is envisioned that the programmer 110 can also include a two-position on/off switch for enabling the programmer 110 to be used with either a one-transmitter design or a two transmitter design. Additionally, the programmer 110 can also include an on-board jumper, i.e., a 0 ohm resistor, to detect the transmitter type input from the transmitter connector for the two-transmitter solution or the switch in the one-transmitter solution.

Controller Board

The controller board of the programmer 110 includes a Digital Signal Processor (DSP), or microprocessor, which controls all the elements of the acoustic monitoring system 100. The DSP is responsible for receiving user input and responding appropriately. It communicates with the display elements to provide visual confirmation of actions and drives a piezo buzzer mounted on the board to provide audible confirmation. The DSP also provides the stepper drive sequence for coil energizing, coordinates signal processing activities and coordinates error detection and response activities. Additionally, the DSP analyzes the signal received from the sensor and correlates it to the command stream provided during the adjustment cycle to establish success or failure of the adjustment.

In addition, controller board provides power to the sensor 130 to generate the acoustic signal. The acoustic signal picked up by the sensor 130 requires filtering and amplification when returned to the controller board. The power required is in the range of approximately 18-35 V, preferably 24 V, at 15 mA. The filtering applied to the signal is a bandpass of 4 kHz-30 kHz. The gain applied will allow full utilization of the range of an analog to digital (A/D) converter. The A/D converter converts the analog sensor signal to a digital data format for further analysis by the signal processor. The controller board also includes sufficient memory necessary to run the system software.

As previously described, the DSP runs a software program which incorporates an algorithm that defines the logical drive sequence required to turn the valve mechanism. Preferably, the sequence is initiated with a stream of 22 commands to turn counterclockwise. This number assures that the mechanism reaches "home" and generates a bang under normal circumstances. There are four signals, one connected to each of the four coils, through the driver described below. As the coils are wired in series as pairs, the signals driving each side of the coil pair will never be "on" at the same time. In a single sequence, the valve mechanism is commanded to move a complete revolution until the mechanism reaches the "home" position. The DSP also analyzes the acoustic signals generated and determines the success or failure of the valve mechanism attaining that position, feeding the information back into the command loop during the adjustment cycle of the valve.

One skilled in the art will appreciate that there are different ways to adjust, or drive a stepper motor. In acoustic monitoring system 100, the coils are energized in "full step" mode during the counterclockwise rotation of the valve mechanism to the "home" position. This means that two windings (all four coils) are energized and are 90° out of phase with each other. The last command given when going to the final setting de-energizes one coil, allowing the stator and rotor magnet to align to a defined position of the valve mechanism. The relationships between commands issued to energize coils and valve mechanism position are defined in Table 1 below.

TABLE 1

Valve Position and Step Commands

| Valve mechanism position | Coils energized for Full step CCW | Coils energized for full step CW | Coil(s) energized for half step CCW |
|---|---|---|---|
| 25 | | 1+/2+ | |
| 30 | | | |
| 35 | 1−/2+ | 1+/2− | 2+ |
| 40 | | | |
| 45 | 1+/2+ | 1−/2− | 1+ |
| 50 | | | |
| 55 | 1+/2− | 1−/2+ | 2− |
| 60 | | | |
| 65 | 1−/2− | 1+/2+ | 1− |
| 70 | | | |
| 75 | 1−/2+ | 1+/2− | 2+ |
| 80 | | | |
| 85 | 1+/2+ | 1−/2− | 1+ |
| 90 | | | |
| 95 | 1+/2− | 1−/2+ | 2− |
| 100 | | | |
| 105 | 1−/2− | 1+/2+ | 1− |
| 110 | | | |
| 115 | 1−/2+ | 1+/2− | 2+ |
| 120 | | | |
| 125 | 1+/2+ | 1−/2− | 1+ |
| 130 | | | |
| 135 | 1+/2− | 1−/2+ | 2− |
| 140 | | | |
| 145 | 1−/2− | 1+/2+ | 1− |
| 150 | | | |
| 155 | 1−/2+ | 1+/2− | 2+ |
| 160 | | | |
| 165 | 1+/2+ | 1−/2− | 1+ |
| 170 | | | |
| 175 | 1+/2− | 1−/2+ | 2− |
| 180 | | | |
| 185 | 1−/2− | 1+/2+ | 1− |
| 190 | | | |
| 195 | 1−/2+ | 1+/2− | 2+ |
| 200 | | 1+/2+ | |
| 205 | | | 1+ |

The number represents which of the two coil pairs is energized and the + and − symbols indicate the direction of current flow. The sequence of commands to return the mechanism to its "home" position is always [1+/2+, 5×(1−/2+, 1−/2−, 1+/2−, 1+/2+), 1−/2+]. The resulting "positions" along the cam, assuming an initial setting of 200 are: 195, 185, 175, 165, 155, 145, 134, 125, 115, 105, 95, 85, 75, 65, 55, 45, 35, 25, "15", no movement, the spring is torsioning, BANG (move to 35, 25 (HOME). The sequence of "15", no motion, BANG (35), 25 will be repeated up to four times, depending on initial setting.

The next command to initiate upward (clockwise) motion is 1+/2+. Upward (clockwise) motion continues in the repeating pattern of 1+/2−, 1−/2−, 1−/2+, 1+/2+ until the desired setting is reached. One of the windings is then turned off leaving the other energized. This allows the stator to align exactly with the rotor mechanism in a defined mechanical position. That coil is then turned off to complete the adjustment cycle. For example, if the selected setting is 70, the following commands will be issued after completion of the home sequence: 1+/2+, 1+/2−, 1−/2−, 1−/2+, 1+/2+ (the position is now "75"), 2+ (coil 1 is turned off, and the position is now "70"), all coils off.

Prior to initiating the adjustment cycle, several aspects of the acoustic monitoring system 100 are monitored when the system 100 is first turned on to confirm functionality before proceeding to an adjustment. For example, the acoustic monitoring system 100 can have a built-in self-test which checks for program integrity, sufficient memory, LCD status, and successful completion of the manufacturing tests. If the self-test detects errors in any of these, a "FATAL" error will appear on the LCD which would prohibit further use of the system 100. Other types of errors, such as with the transmitter connection, amount of current through the coils, transmitter thermistor, or sensor, would generate a "temporary" error message that can be removed once the error is corrected. Failures can be maintained in an error log.

During the adjustment cycle, the controller board also monitors transmitter temperature, which should be below 41° C. If the transmitter temperature is at or above this level, then a message such as "TRANSMITTER COOLING, PLEASE WAIT" would be displayed and the clinician would need to wait for the temperature to drop before proceeding. Such errors would not be recorded. Additionally, the current through the coils is monitored so that they are kept within operating limits (1-3 Amps) during the adjustment cycle. A timer is also used to reset the software every 300 mSec to 500 mSec. This security measure prevents the system 100 from issuing too many adjustment steps without detection during an adjustment cycle. If the reset occurs during an adjustment cycle, an "INCOMPLETE ADJUSTMENT, TRY AGAIN" message is displayed and the user is notified of the error with 3 beeps and a flashing LCD array. This error would be logged into the file. However, if the reset occurs at any time other than during the adjustment cycle, no action is taken and the error is not logged.

The most important function of the controller board and microprocessor is signal analysis and valve movement correlation. As described earlier, acoustic events can be classified in the following categories:

Click—as defined earlier correlates to motion of the spring along the cam

Bang—as defined earlier correlates to motion around the home position

Other—as defined earlier does not meet the required criteria to be classified as "click" or "bang."

The lack of a classified bang event during the home sequence is indicative of an adjustment cycle failure. Where the home position was not reached and therefore the set position is incorrect, the "REPEAT ADJUSTMENT" message is displayed. Presence of a classified bang during the setting sequence is indicative of an adjustment cycle failure. Possible explanations are that the home position was reached during CW movement, in the case of an inverted valve, or there was some mechanical blockage preventing complete upward motion in the case of a stuck valve. The absence of "click" or "bang" events in a functioning system is indicative of incorrect placement of the transmitter relative to the valve. The message "NO SIGNAL, REPEAT ADJUSTMENT" will be displayed to direct the clinician (through clinician training, not as part of the product) to re-locate the transmitter over the valve before trying again.

Power/Driver Board

The power/driver board supports two main functions. The first is the generation of the DC power supplies required by the acoustic monitoring system 100 for operation. The second is placement of the stepper motor drive circuits to allow high current switching of the transmitter coils.

The power/driver board includes a power supply that is responsible for converting the mains power into that required for operation of the acoustic monitoring system 100, isolating the system 100 from effects of line disturbances and the line from effects of the system 100 and isolating the mains power from patient applied and/or user accessible parts. To achieve this isolation, there will be 4000VAC isolation between the mains and any applied part circuitry in conformance with EN60601 standards. The range of inputs is in the range of approximately 90-253 VAC at frequencies of about 47-63 Hz. The input range can be broken up into two (90-132 and 207-253) with automated detection. The ranges stated are as supplied to the product. The design must allow for drops along the wires and filters.

The mains supply will be converted into five DC voltages: 48 V for the coil drive, 5 V for the logic, ±12V for analog circuitry, and 24 V for the acoustic sensor 130. The current and accuracy requirements are outlined in Table 2 below.

TABLE 2

DC Voltage Requirements

| Voltage (VDC) | Current (minimum) | Accuracy (+/−) |
| --- | --- | --- |
| 48 | 5 A | 5% |
| 5 | 1.2 A | 3% |
| ±12 | 150 mA | 3% |
| 24 | 15 mA | 2% |

The power/driver board must comply with EN60601-1-2 standard for EMC compliance, including all associated test standards. Selection of components including line input modules, external connectors and static protection would consider these requirements.

The power/driver board also includes stepper drivers responsible for converting the logic signals received from the microcontroller to high current drive required for creating the magnetic field from the coils. The stepper drivers can be utilized for current monitoring. The current through each coil is returned through a low ohm, high precision resistor to verify that the current is within specification (1-3 A). This allows testing for short or open circuits in the windings before an adjustment cycle is initiated. Additionally, the stepper drivers also prevent cross conduction. Four stepper drive circuits control the current through each of the four coils, which are driven as pairs (i.e., 2 coils combine for one motor winding). Cross conduction prevention is inherent in the drive circuits. Incorporating "wait states" between switching coils provides additional protection in the software. An exemplary wait time of 4 mSec is acceptable.

Transmitter

Two unique transmitters can be provided with the present system: one for package adjustment and one for implant adjustment. As previously discussed, the programmer 110 distinguishes the two from each other based on the wiring of the transmitter cable. The package/viewing transmitter 120 has a viewing hole 124 to allow visualization of the valve mechanism while adjusting in the package, as shown in FIG. 2A. It does not include a sensor and no analysis of signal is performed. Two LEDs can be included to illuminate the packaged valve and indicate that the transmitter is ready to adjust. In contrast, the implant transmitter 130 does not allow visualization. Instead, it contains the sensor 140 to detect the acoustic energies and allow signal analysis to verify the valve movement of an implanted valve. This transmitter can also contain two illuminating LED's to indicate the transmitter is ready to adjust.

The transmitters 120, 130 have two major functions. The first is energizing the stator of the valve stepper motor mechanism based on signals received from the programmer 110. The second major function, in the case of a two-transmitter system, is to provide support and alignment for the acoustic sensor 140 incorporated into the implant transmitter 130. The package/viewing transmitter 120 does not contain an acoustic sensor 140.

A thermistor such as a PT100 can be incorporated in the transmitter to assure that the temperature of the legs 158 does not exceed the requirements for brief patient contact as defined in EN60601. In addition, the cable connecting the transmitter to the programmer will include wiring that allows identification of the type of transmitter, for either implant or package adjustment. Additionally, two LEDs (driven with one control line) on the transmitter can illuminate below the transmitter center to better visualize the valve when in package adjustment mode. The LEDs also provide an indicator to the clinician that the transmitter is "ready" to adjust.

The magnetic field generated by the energized coils is a minimum of 350G when measured in a plane 5 mm below the transmitter feet during the adjustment cycle. The coils are energized in pairs; e.g. 2 coils wired in series make up one stator winding. A "start" key is provided on the transmitter to initiate the adjustment cycle. The magnetic field is focused on the valve by means of 4 legs, preferably formed of stainless steel, which protrude beneath the transmitter base and a stainless steel plate which joins the top of the legs inside the transmitter housing 136. To operate, the transmitter 130 must be placed properly over the valve rotor mechanism to ensure proper adjustment. The sensor 140 must be centered over the mechanism to optimize signal detection. Laboratory testing indicates optimal signal when the sensor assembly is centered within a 5 mm diameter above the valve mechanism.

Sensor

The acoustic sensor 140 is responsible for translating the mechanical (acoustic) energies generated by the valve during an adjustment cycle to electronic signal that can be analyzed for valve position verification. The coupling member 142 which forms the sensor assembly has two major functions. First, the coupling member 142 contacts the patient's skin, thereby connecting the acoustic sensor 140 to the valve implanted in the patient. Second, coupling member 142 isolates the sensor 140 from environmental influences such as vibration and magnetic fields. Coupling of the acoustic sensor 140 to the implanted valve (via the patient's skin) is achieved two ways. The first is the pressure applied between the sensor coupling rod and the patient. The second is the use of ultrasound gel to better match the acoustic impedance. The pressure must be enough to provide contact, but not so much as to squeeze out all the ultrasound gel. The coupling member 142 of the sensor assembly should be allowed 8 mm of travel to accommodate the clinical variations in patient anatomy and valve placement.

The sensor signal is susceptible to mechanical influences such as vibration of the transmitter or hand motion of the clinician, and to electrical influences such as the magnetic field generated by the second transmitter 130. The coupling member 142 must isolate the acoustic sensor 140 from these influences as much as possible. Mechanical isolation is achieved through design and the use of compliant materials such as low durometer o-rings. Electromagnetic isolation is achieved by placing the sensor above the magnetic field focusing plate.

An exemplary method for using the present invention is outlined in Table 3 below. The steps provided below can be used with either the one-transmitter or two-transmitter system; however, the details following are explained as if using a two-transmitter system.

the proper position in its rotation of the stepped motor, an audible sound can be produced to notify the clinician that the valve mechanism is ready to proceed with the next step in the sequence of commands. In the case where the event has not been properly performed, a different audible sound can be generated to notify the clinician of such. The acoustic monitoring system 100 of the present invention is constructed as a feedback loop so that information about an improper event can be fed back to the microprocessor. The programmer 110 can then decide whether to repeat the last command, or shut down the process for further investigation. Alternatively, all

TABLE 3

Valve Adjustment Cycle

| Step | Action |
|---|---|
| 1 | Select desired opening pressure setting on the program unit |
| 2 | Place ultrasound gel on transmitter sensor rod |
| 3 | Locate valve mechanism on patient, using fingers (gloved and ungloved) |
| 4 | Center transmitter sensor rod over valve mechanism, aligning arrow indicators on transmitter head with shunt flow direction |
| 5 | Press START button on transmitter to commence adjustment |
| 6 | Programmer analyzes data and displays the results according to the decision table below: |

| If | Then |
|---|---|
| All required events are accounted for | Display "ADJUSTMENT COMPLETE" with one (1) beep. NOTE: If DISPLAY INITIAL POSITION is enabled AND there were enough events accounted for, the display will read "ADJUSTMENT COMPLETE//INITIAL POSITION/RANGE xx-yy." |
| Not all signal is present | Display "REPEAT ADJUSTMENT" with three (3) beeps and repeat steps 1-7 |
| No signal is present, but hardware is okay | Display "NO SIGNAL < REPEAT ADJUSTMENT" with three (3) beeps and repeat steps 1-7 |
| No signal is present and it is a hardware issue | Display "SENSOR FAILURE" with three (3) beeps and issue alarm (flashing LED array) |

| Step | Action |
|---|---|
| 7 | Remove transmitter from patient wait for signal analysis. Note: 3 beeps indicates a "REPEAT ADJUSTMENT" cycle or an error and the transmitter may remain in place |
| 8 | Clean gel from patient and transmitter. Place transmitter in the attaché case |
| 9 | If a fatal error occurs of if deemed necessary by the clinician, verify the new position by x-ray |

As outlined in Table 3, first ultrasound gel is applied to the patient around the area where the adjustable programmable valve is implanted. Alternatively, the gel may be applied directly to the bottom of the coupling rod. Next the second transmitter 130 is placed over the valve mechanism. Proper placement of the transmitter 130 is crucial to valve rotor adjustment. The sensor 140 should be centered over the valve mechanism to optimize signal detection, preferably within a 5 mm diameter above the valve mechanism.

After the acoustic monitoring device 102 has been properly positioned, the desired sequence of commands can then be initiated. This can be accomplished by pressing a "start" key 132 on the transmitter 130, which then activates the programmer 110 to send out a stream of commands to the transmitter 130. A magnetic field is then generated from energized coils contained within the transmitter 130. This magnetic field, which is focused between the feet 158 of the housing 136, causes the valve mechanism to adjust accordingly. With each movement of the valve mechanism, the acoustic signal generated from that event is then picked up by the acoustic sensor 140. Each of these acoustic signals is in turn translated into an electronic signal and relayed to the programmer 110 where the microprocessor analyzes each signal to determine if the event has occurred as predicted. In the case where the event has been properly performed, i.e., the valve mechanism is in acoustic events can be stored in the programmer and then analyzed in their entirety after the command stream is completed.

The analysis of the sensor signal will determine whether a message of "ADJUSTMENT COMPLETE" for success or "REPEAT ADJUSTMENT" is displayed. Success is determined by the presence of enough acoustic events, relative to command stream, to be confident that the valve is within a predetermined acceptance value (mmH$_2$O) of the selected pressure value. A confidence level better than a predetermined value will be the acceptance criteria. For example, in one embodiment the predetermined value of the confidence level will be better than 99%. In another embodiment the predetermined value of the confidence level will be better than 99.5%. In other words, the false positive rate when the "ADJUSTMENT COMPLETE" is displayed must be less than a predetermined acceptance criteria, for example, less than 1% or less than 0.5%.

If there are not enough acoustic events for confidence that the adjustment cycle was successful, the message "REPEAT ADJUSTMENT" will be displayed. If no acoustic events are identified, AND the hardware seems to be functioning, a message of "NO SIGNAL, REPEAT ADJUSTMENT" is displayed. The distinction is made between these two situations to alert the clinician that, in the second case, the transmitter is probably not over the valve and the transmitter should be relocated.

It is expected that one of the "REPEAT ADJUSTMENT" messages will be displayed as many as one in three tries. The clinician may repeat the adjustment process until satisfied. It is expected the incidence of more than three successive tries will be less than 1%, as it is likely that the valve mechanism is stuck, is too deep, or is inverted.

While the present system 100 has been described for use in verifying proper valve mechanism position in an adjustable programmable valve, in general the present invention provides an apparatus and method which is suitable for analyzing an acoustic signal to identify the differences between the signal generated by any implanted device and the signal generated by the tissue in which the device is implanted. That is, the present invention can be broadly directed to diagnostic monitoring of an implanted device in the body (auscultation). The acoustic signal received can provide information about the implanted device with or without interrogation of the device and without any invasive procedures. The acoustic signal generated can be an intrinsic signature of the operating device. In the particular case of a shunt valve, some potential detection events can also include valve opening and/or closing pressure, or determination of fluid flow rate and pressure through the device (i.e., cerebral spinal fluid flow through a shunt and intracranial pressure measurements). Yet another example would be to use acoustic signatures to determine whether or not an implanted device is properly functioning.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An acoustic monitoring device for verifying the pressure setting of a valve mechanism in an implantable device having a plurality of adjustable valve settings, comprising:
    an extracorporeal housing having a top surface, a bottom surface, and a central opening;
    a transmitter contained within the housing having a plurality of electromagnetic coils configured to generate an energy field sufficient to effect movement of the valve mechanism of the implantable device;
    an acoustic sensor disposed within the central opening in the housing and electronically coupled to the transmitter for detecting acoustic signals generated by the valve mechanism during an adjustment cycle; and
    a microprocessor configured to compare the detected acoustic signals to expected acoustic signals to verify the pressure setting of the valve mechanism.

2. The device of claim 1, wherein the energy field is a magnetic field.

3. The device of claim 1, further including a tubular coupling member extending through the central opening and beyond the bottom surface of the housing.

4. The device of claim 3, wherein the tubular coupling member is configured to contact a patient's skin.

5. The device of claim 3, wherein the acoustic sensor is selectively disposed within the tubular coupling member.

6. The device of claim 5, wherein the acoustic sensor is electromagnetically isolated from the transmitter.

7. The device of claim 5, further including mechanical isolating pads surrounding the inner surface of the tubular coupling member.

8. The device of claim 5, wherein the sensor is seated on top of the tubular coupling member.

9. The device of claim 5, further including a plurality of feet extending from the bottom surface of the housing to focus the generated energy field on the valve mechanism.

10. The device of claim 3, wherein the acoustic sensor is adapted to be inserted into the housing after the housing is placed over the valve mechanism.

11. The device of claim 3, wherein the tubular coupling member is held in springing engagement with respect to the housing and self-adjusts to conform to the patient's anatomy.

12. The device of claim 1, further including a power source for driving the energy field.

13. The device of claim 1, further including a signal amplifier, a digitizing filter, and a data storage unit for transmitting any detected acoustic signals to a programmer for analysis.

14. The device of claim 13, further comprising means for wireless communication between the acoustic monitoring device and the programmer.

15. The device of claim 14, wherein the means for wireless communication comprises a wireless communication transmitter connected to the transmitter of the acoustic monitoring device.

16. An acoustic monitoring system for verifying the pressure setting of a valve mechanism in an implantable device having a plurality of adjustable valve settings, comprising:
    an extracorporeal device for adjusting an opening pressure of the valve mechanism;
    an extracorporeal transmitter having a central opening formed therein and configured to generate an energy field sufficient to cause movement of the valve mechanism; and
    an acoustic sensor disposed within the central opening in the transmitter and electrically coupled to the transmitter for detecting acoustic signals generated by the valve mechanism during and adjustment cycle;
    wherein the transmitter communicates the detected acoustic signals to the device for analysis, and
    wherein the device includes a microprocessor configured to compare the detected acoustic signals to expected acoustic signals to verify the pressure setting of the valve mechanism.

17. The system of claim 16, wherein the device includes a microprocessor that translates any detected acoustic signals into information for determining the success or failure of the adjustment cycle.

18. The system of claim 17, wherein the microprocessor classifies the acoustic signals into signals indicative of movements and signals indicative of positions.

19. The system of claim 18, wherein the microprocessor compares the actual streams of acoustic signals to an expected stream of acoustic signals to determine the success or failure of the adjustment cycle.

* * * * *